United States Patent
Berger et al.

(10) Patent No.: US 6,683,220 B2
(45) Date of Patent: Jan. 27, 2004

(54) PROCESS FOR THE PREPARATION OF OPTICALLY PURE OR ENRICHED RACEMIC TETRALONE

(75) Inventors: Laurent Berger, La Valla en Gier (FR); Raphael Duval, Notre Dame de Gravenchon (FR); Philippe Taillasson, Saint Laurent d'Agny (FR); Ingo Weber, Lyons (FR); Alexander Wick, Saint Nom-la Bretéche (FR)

(73) Assignee: Pfizer, Inc., New York, NY (US)

( * ) Notice: Subject to any disclaimer, the term of this patent is extended or adjusted under 35 U.S.C. 154(b) by 0 days.

(21) Appl. No.: 10/246,796

(22) Filed: Sep. 18, 2002

(65) Prior Publication Data

US 2003/0105364 A1 Jun. 5, 2003

Related U.S. Application Data

(60) Provisional application No. 60/335,429, filed on Oct. 31, 2001.

(51) Int. Cl.[7] .................. C07C 45/00; C07C 233/00; C07C 211/00
(52) U.S. Cl. .................. 568/314; 568/315; 568/316; 568/321; 564/222; 564/308
(58) Field of Search .................. 568/314, 315, 568/316, 321; 564/222, 308

(56) References Cited

U.S. PATENT DOCUMENTS

| 5,403,898 | A | * | 4/1995 | Bradshaw et al. |
| 5,639,824 | A | * | 6/1997 | Okamoto |
| 5,750,794 | A | * | 5/1998 | Quallich |
| 6,136,198 | A | * | 10/2000 | Adam et al. |
| 6,444,854 | B1 | * | 9/2002 | Dapremont et al. |

* cited by examiner

Primary Examiner—Johann Richter
Assistant Examiner—Sikarl A. Witherspoon
(74) Attorney, Agent, or Firm—William J. Sapone; Coleman Sudol Sapone, P.C.

(57) ABSTRACT

A process for producing substantially optically pure sertraline utilizes chromatographic separation on a solid stationary chiral phase of spherical clay particles having an interlayer containing an optically pure metal-organic complex, and a liquid mobile phase preferably containing at least methyl acetate. The liquid mobile phase is preferably free of acetonitrile. The process is operable at temperatures above 40° C.

17 Claims, No Drawings

PROCESS FOR THE PREPARATION OF OPTICALLY PURE OR ENRICHED RACEMIC TETRALONE

CROSS REFERENCE TO RELATED APPLICATION

This application claims priority in U.S. Provisional patent application No. 60/335,429 filed Oct. 31, 2001.

BACKGROUND OF THE INVENTION

This invention relates to a chromatographic process for obtaining optically pure tetralone as an intermediate in the preparation of optically pure sertraline. Sertraline is used in the synthesis of Zoloft, a drug currently marketed for the treatment of depression, as discussed in the U.S. Pat. Nos. 4,536,518, 5,196,607, 5,442,116 and 4,777,288, all incorporated by reference. Various processes for preparing Sertraline are described in the above patents. Typically, there is a resolution of a racemic mixture of sertraline at the later stages of the process which has the disadvantage of requiring an undesired enantiomer to be carried through several of the processing steps. It is preferred and would be a significant advantage if an enantiomerically pure tetralone were used as a starting material in the preparation of optically pure sertraline to substantially limit the production of the undesirable enantiomer of sertraline, thus avoiding a final separation step.

To produce Zoloft (sertraline hydrochloride) in an efficient way, separation of the cis-(1S, 4S) enantiomer from cis-(1R, 4R) enantiomer of sertraline-tetralone is required. In PCT publication number WO99/57089, a process for producing an enantiomerically pure or optically enriched sertraline-tetralone is described utilizing continuous chromatography. Key to the processing is the utilization of a derivitized polysaccharide solid chiral stationary phase and a liquid mobile phase preferably containing acetonitrile.

While an available route to achieving optically pure sertraline, the process utilizes a solid chiral stationary phase which has limited utility at temperatures above 40° C. Acetonitrile is an expensive solvent, that is also environmentally undesirable to use due to its' toxicity. The cost of production utilizing such a process is thus high, and may not be sufficiently economically attractive so as to find utilization in the preparation of optically pure tetralone. Consequently the search continues for processes for producing optically pure or enriched sertraline at low cost and with optimized productivity.

SUMMARY OF THE INVENTION

A process for chromatographically obtaining substantially enantiomerically pure chiral tetralone from a mixture of two tetralone enantiomers comprises providing a liquid mobile phase comprising at least one solvent; providing a solid stationary chiral phase comprising an inorganic carrier loaded with an optically pure metal-organic complex; and, chromatographically separating the mixture to obtain at least one substantially enantiomerically pure tetralone. The solvent used may be selected from the group consisting of lower alcohols such as methanol, ethanol, propanol, isopropanol, butanol; acetates and propionates of these alcohols; ketones such as acetone, butanone, isopropylmethylketone; ethers, such as diethyl ether, diisopropyl ether, tertbutylmethyl ether; tetrahydrofuran; dioxane; alkanes such as pentane, hexane, heptane, cyclohexane, cycloheptane, benzene, toluene, xylene; halogenated lower alkanes such as methylene chloride, chloroform, chlorobenzene, fluorinated lower alkanes, acetonitrile, and combinations of these. The solvent is preferably a mixture of methanol and methyl acetate. The separation of the mixture is preferably conducted at a temperature of from about 40EC to about 80EC. In the inorganic carrier material (silica gel, clay, etc.), the metal complexing cations are selected from metals from the group consisting of nickel, osmium, ruthenium, platinum, cobalt, iron, copper and chromium, with ruthenium complexing cations preferred. The organic part of the metal-organic complex consists of aromatic nitrogen-containing heterocycles which confer chirality to the complex. Such complexes can be obtained in optically pure form from their racemates by known methods. The preferred heterocycles are 2,3-bipyridines and 1,10-phenanthrolines. The inorganic carrier is preferably a spherical clay material. The inorganic carrier may have a particle size of from about 5 to 30 $\mu$m, and also may be hydrophobically treated. In one embodiment, the liquid mobile phase used is a supercritical fluid, such as supercritical $CO_2$, and a polar solvent selected from the group consisting of methanol, ethanol, THF, dichloroethane, acetone, methyl acetate and ethyl acetate. The chromatographic process may use single column chromatography, or multicolumn chromatography such as simulated moving bed chromatography, or non-steady state continuous chromatography. In one embodiment, at least one substantially pure tetralone enantiomer is a preferred enantiomer and a second of the two enantiomers in the mixture is an undesired enantiomer, the solid stationary phase having a chiral orientation for retaining the undesired enantiomer.

Using a mobile phase preferably free of acetonitrile and containing methanol reduces cost and eases environmental concerns. The use of a clay carrier having an interlayer of optically active metal-organic complex cations therein, enables processing at higher temperatures, of from about 40 to 80° C., which leads to higher solubility and higher productivity without detrimentally affecting the enantiomer separation. According to the present invention, optically pure or enriched tetralone can be obtained in an environmentally acceptable fashion at higher yield with reduced cost, as compared to the prior art, enabling the production of optically pure sertraline with less process steps.

DETAILED DESCRIPTION OF THE INVENTION

The process of the present invention can utilize any continuous chromatographic method for separating racemic tetralone so as to produce optically pure or enriched tetralone for the production of sertraline, such as single column chromatography or simulated moving bed (SMB) chromatography. While a simulated moving bed process may be used, a preferred chromatographic method is described in U.S. Pat. No. 6,136,198, where a non-steady state continuous separation process can be used which varies the length of given zones represented by column sections during the chromatographic separation to increase efficiency.

In either case, the process for obtaining enantiomerically pure or optically enriched tetralone utilizes one or more columns packed with a solid stationary chiral phase which preferentially absorbs a first enantiomer (the more strongly retained enantiomer) from a feed containing the enantiomer mixture. Ports are provided for introducing the feed mixture, for introducing a desorbant liquid mobile phase, for removing a raffinate containing the second enantiomer (the less strongly retained enantiomer) and for removing an extract which contains the desorbed more strongly retained enantiomer. Multiple columns are preferably used and connected to each other from a feed end to an outlet end. While the outlet end could be connected to the feed end to provide a continuous recycle, recycle is unnecessary in the preferred process of the invention.

The liquid mobile phase is selected from lower alcohols such as methanol, ethanol, propanol, proponal, isopropanol, butanol; acetates, and propionates of these alcohols; ketones such as acetone, butanone, isopropyl-methylketone, ethers, such as diethyl ether, diispropyl ether, tertbutylmethyl ether; tetrahydrofuran; dioxane; alkane such as pentane, hexane, heptane, cyclohexane, cycloheptane, benzene, toluene, xylene; halogenated lower alkanes such as methylene chloride, chloroform, chlorobenzene, fluorinated lower alkanes, and combinations of these. While acetonitrile may be used, in certain circumstances, it is generally not a preferred solvent.

Of the various solvents, a methyl acetate based liquid mobile phase is preferred which may comprise methyl acetate alone or methyl acetate in combination with one or more of the solvents listed above. More preferably, methyl acetate or a methanol/methyl acetate mixture is used. The most preferred liquid mobile phase is methanol/methyl acetate having a ratio in the range of 0 to 100, more preferably 70 to 30 and most preferably 85 to 15.

This particular liquid mobile phase has the advantage of being of low cost relative to acetonitrile, is less toxic and is fully compatible with the selected solid chiral phase and temperature.

The solid chiral phase is composed of an inorganic carrier (silica gel, clay, zeolite, etc) which is loaded with a cationic optically pure metal-organic complex which binds strongly to the silicate anions present in the carrier material. Preferably, the solid chiral phase is composed of spherical clay particles in which cations having an ion exchange capability are incorporated in an interlayer. Preferably, a silanizing agent is used to hydrophobically treat the material to inhibit water swelling and to render the solid phase material water resistant and less susceptible to contamination during processing. Such a solid phase material is more durable, the additional endurance increasing the useful life of the solid phase, increasing efficiency and productivity relative to the amount of solid phase consumed. Increased on-line time can be expected, as the solid chiral phase is more resilient and less sensitive to process variations. In addition, the clay based solid chiral phase has the capability of operating at temperatures above 40° C., up to about 80° C., which can significantly increase productivity, particularly in comparison to polysaccharide. While the temperature may range from 0° to 100° C., the preferred range is from 40° C. to 80° C., and more preferably about 50–60° C.

One type of spherical clay chromatographic separation material useable as a solid chiral phase in the inventive process is described in U.S. Pat. No. 5,145,578. A hydrophobically treated spherical clay chromatographic separation material is described in Japanese Kokai No. 8-201366. Such materials are commercially available from Shiseido Co. Ltd., Tokyo, Japan.

The carrier particles have a metal-organic complex cation interlayer with the metal selected from the group consisting of nickel, osmium, ruthenium, platinum, cobalt, iron, copper and chromium. In a preferred embodiment, the metal complex is based on a ruthenium complex. For example, a spherical clay chiral separation material known as Ceramosphere RU-1, available from Shiseido may be used. A hydrophobically treated spherical clay chiral separation material that may be used is Ceramosphere RU-2, also using ruthenium metal complexing cations. RU-2 is preferred because it is more water resistant, and thus more tolerant of processing variations.

The spherical clay material should have a particle size of at least 5 microns, more preferably up to about 50 microns, with a range of about 10 to 30 microns preferred. Also, it is preferred that the material be processed to have a chiral orientation selected to strongly retain the least preferred enantiomer of the tetralone so that the preferred enantiomer is recovered in the raffinate, as this promotes higher purity of the preferred enantiomer which is also the first to exit the column. In such a case, the less retained/desired enantiomer may be recovered at the desired optical purity of 95 to 99.9% in the raffinate stream. The more retained/undesired enantiomer retained by the solid chiral phase, is extracted later on with the liquid mobile phase, and collected in the extract stream. It is possible to racemize the undesired enantiomer and to supply this as feed, to increase the overall process yield.

While a simulated moving bed process may be used, a non-steady state dynamic chromatographic separation process is preferred. By non-steady state process is meant the use of a chromatographic separation system where the zones between inlet and outlet ports are variable in length at different times such that the equivalent solid flow rate differs with respect to the inlet and outlet ports. In a SMB process, all the inlet and outlet ports are shifted substantially simultaneously, to simulate counter-current flow between the liquid phase and the solid phase. In the non-steady state system, there is an asynchronus shifting of the inlet and outlet ports so that the zone lengths are not constant in time. This process is described in U.S. Pat. No. 6,136,198, incorporated by reference and referred to hereafter as the "Varicol™" process.

Such a process produces optically pure or enriched chiral tetralone with less columns, reducing the quantity of solid phase yet with higher purity as compared to a conventional SMB process.

In one embodiment of the invention, a five to six column-four variable zone Varicol™ system is used together with the selected liquid and solid phase materials discussed above, which may be operated with or without recycle, and at temperatures at or above 40° C. The zones vary in length during operation, and have an average rather than fixed length in a given operation cycle. In another embodiment, a three column-three variable zone Varicol™ system is used, a system which cannot be utilized in a SMB process, as at least four columns with four zones are necessary to simulate the true moving bed system. In the three or five column systems, the quantity of solid phase material is reduced yet yields and through-puts obtained that are comparable to or better than those achieved with a conventional SMB process.

In another embodiment of the invention, a liquid phase is chosen which is a mixture of a supercritical fluid and a polar solvent, for example supercritical $CO_2$ and a polar solvent selected from the group consisting of methanol, ethanol, THF, dichloroethane, acetone, methyl acetate and ethyl acetate. Generally a solvent containing from 20 to 60% supercritical $CO_2$ mixed with one of the solvents given above provides a suitable liquid mobile phase. Using such a mixture eases product recovery and solvent reclamation.

EXAMPLES

The following 4 examples were undertaken using an SMB process, though the invention is not limited to SMB processing, as discussed above. However the results are believed representative of the benefits obtained using the method of the invention.

Example 1

OPERATING PARAMETERS

| | |
|---|---|
| Chiral Solid Phase | RU2-lambda 27 μm |
| Mobile Phase: | methyl acetate/methanol: 50/50 v/v |
| Column Length: | 11 cm |
| Column I.D.: | 48 mm |
| Number of Columns | 6 |
| Feed concentration: | 12.5% w/v |
| Eluent Flow Rate: | 249 ml/min |
| Feed Flow Rate: | 40 ml/min |
| Flow Rate in Zone 1: | 425 ml/min |
| Extract Flow Rate: | 237 ml/min |
| Raffinate Flow Rate: | 52 ml/min |
| Period: | 0.95 min |
| Temperature: | 50° C. |
| Operating Pressure: | 25 bar |

SMB PERFORMANCE (PILOT SCALE)

| | |
|---|---|
| Less retained enantiomer purity (S-Tetralone %): | 98.9% |
| Less retained enantiomer recovery yield (S-Tetralone %): | 97.8% |
| Calculated volume of eluent necessary (l/g enantiomer): | 0.102 l/g |
| Productivity (kg enantiomer pr day per kg CSP) | 3.0 kg/kg CSP/day |
| Amount of feed to be processed (kg enantiomer recovered) | 2.05 kg |
| Amount of product to be racemized (kg per kg enantiomer recovered: | 1.05 kg |

Example 2

OPERATING PARAMETERS

| | |
|---|---|
| CSP | RU2-lambda 27 μm |
| Mobile Phase: | methyl acetate/methanol: 50/50 v/v |
| Column Length: | 11 cm |
| Column I.D.: | 48 mm |
| Number of Columns | 6 |
| Feed concentration: | 12.5% w/v |
| Eluent Flow Rate: | 261 ml/min |
| Feed Flow Rate: | 50 ml/min |
| Flow Rate in Zone 1: | 435 ml/min |
| Extract Flow Rate: | 241 ml/min |
| Raffinate Flow Rate: | 70 ml/min |
| Period: | 0.95 min |
| Temperature: | 50° C. |
| Operating Pressure: | 25 bar |

SMB PERFORMANCE (PILOT SCALE)

| | |
|---|---|
| Less retained enantiomer purity (S-Tetralone %): | 98.1% |
| Less retained enantiomer recovery yield (S-Tetralone %): | 92.4% |
| Calculated volume of eluent necessary (l/g enantiomer): | 0.091 l/g |
| Productivity (kg enantiomer pr day per kg CSP) | 3.5 kg/kg CSP/day |
| Amount of feed to be processed (kg enantiomer recovered) | 2.16 kg |
| Amount of feed to be racemized (kg per kg enantiomer recovered: | 1.16 kg |

Example 3

OPERATING PARAMETERS

| | |
|---|---|
| CSP | RU2-lambda 17 μm |
| Mobile Phase: | methyl acetate/methanol: 70/30 v/v |
| Column Length: | 8 cm |
| Column I.D.: | 48 mm |
| Number of Columns | 6 |
| Feed concentration: | 20% w/v |
| Eluent Flow Rate: | 141 ml/min |
| Feed Flow Rate: | 25 ml/min |
| Flow Rate in Zone 1: | 255 ml/min |
| Extract Flow Rate: | 134 ml/min |
| Raffinate Flow Rate: | 32 ml/min |
| Period: | 0.85 min |
| Temperature: | 50° C. |
| Operating Pressure: | 30 bar |

SMB PERFORMANCE (PILOT SCALE)

| | |
|---|---|
| Less retained enantiomer purity (S-Tetralone %): | 99.5% |
| Less retained enantiomer recovery yield (S-Tetralone %): | 83.5% |
| Calculated volume of eluent necessary (l/g enantiomer): | 0.068 l/g |
| Productivity (kg enantiomer pr day per kg CSP) | 3.8 kg/kg CSP/day |
| Amount of feed to be processed (kg enantiomer recovered) | 2.4 kg |
| Amount of feed to be racemized (kg per kg enantiomer recovered: | 1.4 kg |

Example 4

OPERATING PARAMETERS

| | |
|---|---|
| Column: CSP | RU2-lambda 17 um |
| Mobile Phase: | methyl acetate/methanol: 70/30 v/v |
| Column Length: | 8 cm |
| Column ID.: | 48 mm |
| Number of Columns | 5 |
| Feed concentration: | 20% w/v |
| Eluent Flow Rate: | 176 ml/min |
| Feed Flow Rate: | 35 ml/min |
| Flow Rate in Zone 1: | 354 ml/min |
| Extract Flow Rate: | 176 ml/min |
| Raffinate Flow Rate: | 35 ml/min |
| Period: | 0.60 min |
| Temperature: | 50° C. |
| Operating Pressure: | 35 b |

SMB PERFORMANCE (PILOT SCALE)

| | |
|---|---|
| Less retained enantiomer purity (S-Tetralone %): | 99.5% |
| Less retained enantiomer recovery yield (S-Tetralone %): | 75% |
| Calculated volume of eluent necessary (l/g enantiomer): | 0.067 l/g |
| Productivity (kg enantiomer pr day per kg CSP) | 5.6 kg/kg CSP/day |
| Amount of feed to be processed (kg enantiomer recovered) | 2.65 kg |
| Amount of feed to be racemized (kg per kg enantiomer recovered: | 1.65 kg |

Example 5 Using a Varicol™ Process

OPERATING PARAMETERS

| | |
|---|---|
| Column: CSP | RU2-lambda 17 um |
| Mobile Phase: | methyl acetate/ |

-continued

| | |
|---|---|
| | methanol: 81/19 v/v |
| Column Length: | 8 cm |
| Column ID.: | 48 mm |
| Number of Columns | 6 |
| Average number of columns per zone: | 0.75/1.5/3.25/0.5 |
| Feed concentration: | 25% w/v |
| Eluent Flow Rate: | 220 ml/min |
| Feed Flow Rate: | 30 ml/min |
| Flow Rate in Zone 1: | 365 ml/min |
| Extract Flow Rate: | 205 ml/min |
| Raffinate Flow Rate: | 45 ml/min |
| Period: | 0.65 min |
| Temperature: | 50° C. |
| Operating Pressure: | 35 b |
| Varicol ™ PERFORMANCE (PILOT SCALE) | |
| Less retained enantioner purity (S-Tetralone %): | 99.5% |
| Less retained enantioner recovery yield (S-Tetralone %): | 83% |
| Calculated volume of eluent necessary (l/g enantiomer): | 0.071 l/g |
| Productivity (kg enantiomer pr day per kg CSP) | 5.6 kg/kg CSP/day |
| Amount of feed to be processed (kg enantiomer recovered) | 2.4 kg |
| Amount of feed to be racemized (kg per kg enantiomer recovered: | 1.4 kg |

Table 1 summarizes the results of various tests using the spherical clay material as the chiral solid phase, at temperatures from 40–60° C., using methyl acetate/methanol, from 30–65% methyl acetate, and at pressures from about 5 to 78 bar. A six column SMB process (48 mm diameter) was used for test purposes.

TABLE 1

| No. | Particle Size (μm) | Temperature (CE) | Methylacetate (%) | Pressure (bar) | Concentration of racemate injected (g/L) |
|---|---|---|---|---|---|
| 1 | 5 | 40 | 100 | 72 | 280 |
| 2 | 5 | 40 | 90 | 74 | 260 |
| 3 | 5 | 40 | 80 | | 250 |
| 4 | 5 | 40 | 75 | | 200 |
| 5 | 5 | 40 | 50 | 78 | 150 |
| 6 | 10 | 55 | 70 | 17 | 260 |
| 7 | 10 | 55 | 65 | 17 | 150 |
| 8 | 10 | 55 | 50 | 16 | 200 |
| 9 | 27 | 55 | 35 | 5 | 125 |
| 10 | 27 | 50 | 35 | 5 | 100 |
| 11 | 27 | 60 | 30 | 5 | 150 |
| 12 | 27 | 55 | 30 | 5 | 125 |
| 13 | 27 | 50 | 30 | 5 | 100 |
| 14 | 27 | 40 | 30 | 5 | 90 |
| 15 | 27 | 60 | 40 | 5 | 175 |
| 16 | 27 | 55 | 40 | 5 | 125 |
| 17 | 27 | 50 | 40 | 5 | 100 |
| 18 | 27 | 50 | 45 | 5 | 100 |
| 19 | 27 | 55 | 45 | 5 | 150 |
| 20 | 27 | 55 | 50 | 5 | 175 |
| 21 | 27 | 40 | 50 | 5 | 90 |
| 22 | 27 | 50 | 50 | 5 | 125 |
| 23 | 17 | 50 | 65 | 10 | 175 |
| 24 | 17 | 50 | 60 | 10 | 175 |
| 25 | 17 | 50 | 55 | 10 | 175 |
| 26 | 17 | 50 | 50 | 10 | 175 |
| 27 | 17 | 50 | 45 | 10 | 175 |

TABLE 1-continued

| No. | Bed length (cm) | SMB(*) Production (Kg/day) | Specific productivity (Kg/Kg/day) | PURITY Raffinate (%) | PURITY Extract (%) |
|---|---|---|---|---|---|
| 1 | 1.50 | 3.90 | 23.93 | 99.26 | 99.37 |
| 2 | 1.30 | 4.58 | 32.42 | 99.29 | 98.12 |
| 3 | 1.30 | 4.74 | 33.56 | 99.19 | 99.30 |
| 4 | 1.30 | 5.28 | 37.41 | 98.99 | 99.43 |
| 5 | 1.30 | 3.48 | 24.67 | 99.53 | 99.89 |
| 6 | 3.80 | 5.66 | 13.73 | 99.00 | 99.17 |
| 7 | 4.00 | 4.55 | 10.47 | 99.12 | 99.17 |
| 8 | 4.00 | 5.32 | 12.24 | 99.08 | 99.65 |
| 9 | 12.00 | 3.70 | 2.84 | 99.41 | 99.43 |
| 10 | 12.25 | 3.70 | 2.78 | 99.13 | 99.57 |
| 11 | 10.75 | 4.23 | 3.62 | 99.16 | 99.47 |
| 12 | 9.50 | 3.68 | 3.57 | 99.02 | 98.18 |
| 13 | 12.00 | 3.65 | 2.80 | 99.23 | 99.45 |
| 14 | 10.25 | 2.88 | 2.59 | 99.41 | 99.15 |
| 15 | 11.25 | 4.60 | 3.77 | 99.09 | 99.49 |
| 16 | 12.00 | 3.50 | 2.69 | 99.17 | 99.55 |
| 17 | 13.00 | 3.47 | 2.46 | 99.16 | 99.33 |
| 18 | 12.75 | 3.34 | 2.42 | 99.06 | 99.68 |
| 19 | 12.25 | 3.35 | 2.52 | 99.19 | 99.48 |
| 20 | 14.75 | 2.48 | 1.55 | 99.33 | 99.55 |
| 21 | 13.50 | 2.92 | 1.99 | 99.32 | 98.93 |
| 22 | 13.75 | 2.99 | 2.01 | 99.25 | 99.12 |
| 23 | 5.90 | 8.30 | 12.95 | 99.20 | 98.93 |
| 24 | 5.50 | 7.10 | 11.88 | 99.16 | 99.07 |
| 25 | 5.50 | 8.06 | 13.50 | 99.21 | 99.32 |
| 26 | 5.50 | 8.17 | 13.69 | 99.28 | 99.41 |
| 27 | 5.10 | 6.66 | 12.03 | 99.35 | 98.95 |

As seen from examples 1–5 and Table 1, high purity enantiomer is obtained with reduced solvent volume and increased productivity, while operating at relatively high temperatures, above 40° C. Utilizing a non-steady state Varicol™ chromatographic separation process may result in further increases in productivity as the quantity of solid stationary phase may be reduced with the number of columns optimized.

Other solvents can be used in the inventive process as illustrated in the following Table 2.

| C.P.S. | Solvent 1 | % | Solvent 2 | % | Temp. (° C.) | Width of two peak (min) | Injected (mg) | Productivity (kg/kg cps/day) |
|---|---|---|---|---|---|---|---|---|
| RU-1 | Acetonitrile | 100 | — | 0 | 30 | 3.4 | 12.5 | 1.32 |
| " | Acetone | 100 | — | 0 | 40 | 2 | 12 | 2.16 |
| " | Ethyl acetate | 100 | — | 0 | 40 | 4.5 | 50 | 4.00 |
| " | Ethyl acetate | 100 | — | 0 | 60 | 4 | 50 | 4.5 |
| " | 2- | 100 | — | 0 | 40 | 2 | 10 | 1.80 |

-continued

| C.P.S. | Solvent 1 | % | Solvent 2 | % | Temp. (° C.) | Width of two peak (min) | Injected (mg) | Productivity (kg/kg cps/day) |
|---|---|---|---|---|---|---|---|---|
| " | butanone Ethyl acetate | 75 | Methanol | 25 | 40 | 4.5 | 50 | 4.00 |
| " | Ethyl acetate | 50 | Methanol | 50 | 40 | 8 | 70 | 3.15 |
| RU-2 | 2-butanone | 100 | — | 0 | 40 | 1.4 | 25 | 6.43 |
| " | 2-butanone | 75 | Methanol | 25 | 40 | 2 | 40 | 7.20 |
| " | 2-butanone | 25 | Methanol | 75 | 40 | 11 | 112 | 3.67 |
| " | Ethanol | 100 | — | 0 | 40 | 15 | 80 | 1.92 |
| " | Ethanol | 25 | Ethyl acetate | 75 | 40 | 1.9 | 25 | 4.74 |

In utilizing a supercritical fluid mixture as the liquid mobile phase, further productivity increases are obtained although there are increased requirements for the equipment when handling a supercritical fluid.

An estimate of the productivity increase was made utilizing 140 milligrams of racemate injected into a HPLC column every 5 minutes, with the liquid phase comprised of 30% supercritical $CO_2$, 70% ethyl acetate. The solid stationary phase used was Ceramospher Ru-1. It was determined that the quantity of racemate purified would be 7.3 kilograms per liter of support per day, as compared to using methyl acetate/methanol and Ceramospher RU-2. The HPLC analytical examples are believed representative and serve as a model for SMB processing, and can be used for predicting productivity. The results are illustrated in the following Table 3:

TABLE 3

| | Supercritical | HPLC |
|---|---|---|
| Column Solid Phase (CSP) | Ru-1 | Ru-2 |
| Diameter | 4.6 mm | 4.6 mm |
| Length | 25 cm | 25 cm |
| Granulometry | 5 µm | 5 µm |
| Solvent | $CH_3COOC_2H_5/CO_2$ | $CH_3COOCH_3/CH_3OH$ |
| Ratio | 70/30 | 80/20 |
| Pressure | 150 bar | 70 bar |
| Temperature | 50° C. | 40° C. |
| Productivity | 7.3 kg/kg support/day | 4.3 kg/kg support/day |

It can be seen from the comparison that RU-1 can be used with a supercritical fluid mixture as the liquid mobile phase, just as well as using RU-2 when not in the supercritical mode. The productivity is at lease double when operating in the supercritical mode, and this is without the further improvements to be achieved with utilization of the Varicol™ process. Consequently, the most economic solution may lie in utilizing a supercritical fluid mixture. However, supercritical fluids need not be used to obtain the benefits of the present invention, as a substantial improvement is achieved by using a spherical clay material such as RU-2 with the liquid phases and processing described above and where the additional equipment requirements for use of supercritical fluids are not desired.

The present invention provides a process for producing optically pure tetralone as an intermediate in the production of optically pure sertraline, to avoid a final chiral separation of sertraline, producing optically pure tetralone using a chromatographic process that is capable of operating at high temperatures, that is above 40° C., to increase separation efficiency. The inventive process preferably uses a liquid mobile phase free of acetonitrile, and a solid chiral phase that is less sensitive to the presence of contaminants such as water or acids, and which is free of polysaccharides. Optionally utilizing non steady state moving bed chromatography reduces the amount of solid chiral phase and optimizes processing efficiency by dynamically varying the bed length during the separation. In another embodiment, optically pure or enriched tetralone is obtained using a supercritical fluid as a portion of the liquid mobile phase.

While preferred embodiments of the present invention have been shown and described, it will be understood by those skilled in the art that various changes or modifications can be made without varying from the scope of the invention.

What is claimed is:

1. A process for chromatographically resolving substantially enantiomerically pure chiral tetralone from a mixture of two tetralone enantiomers comprising:

providing a liquid mobile phase comprising at least one solvent;

providing a solid stationary chiral phase comprising an inorganic carrier having an optically pure metal-organic complex; and, chromatographically separating the mixture to obtain at least one substantially enantiomerically pure tetralone.

2. The process of claim 1 wherein the solvent is selected further comprising selecting the solvent from the group consisting of lower alcohols such as methanol, ethanol, propanol, isopropanol, butanol; acetates and propionates of these alcohols; ketones such as acetone, butanone, isopropyl-methylketone; ethers, such as diethyl ether, diisopropyl ether, tertbutylmethyl ether; tetrahydrofuran; dioxane; alkane such as pentane, hexane, heptane, cyclohexane, cycloheptane, benzene, toluene, xylene; halogenated lower alkanes such as methylene chloride, chloroform, chlorobenzene, fluorinated lower alkanes, acetonitrile, and combinations therein.

3. The process of claim 1 wherein the separation of the mixture is conducted at a temperature of from about 40° C. to about 80° C.

4. The process of claim 1 wherein the solvent is a mixture of methanol and methyl acetate.

5. The process of claim 1 wherein the metal complexing cations are selected from metals from the group consisting of nickel, osmium, ruthenium, platinum, cobalt, iron, copper and chromium.

6. The process of claim 1 wherein the metal complexing cations are ruthenium complexing cations.

7. The process of claim 1 wherein the solid stationary chiral phase comprises a hydrophobically treated spherical clay material.

8. The process of claim 1 wherein the solid stationary chiral phase has a particle size of from about 5 to 30 $\mu$m.

9. The process of claim 1 wherein the liquid mobile phase further comprises a supercritical fluid.

10. The process of claim 1 wherein the liquid mobile phase contains supercritical $CO_2$ and the solvent is a polar solvent selected from the group consisting of methanol, ethanol, THF, dichloroethane, acetone, methyl acetate and ethyl acetate.

11. The process of claim 1 further comprising chromatographically separating the mixture using single column chromatography.

12. The process of claim 1 further comprising chromatographically separating the mixture using simulated moving bed chromatography.

13. The process of claim 1 further comprising chromatographically separating the mixture using multicolumn non-steady state continuous chromatography.

14. The process of claim 1 wherein at least one substantially pure tetralone enantiomer is a preferred enantiomer and a second of the two enantiomers in the mixture is an undesired enantiomer, and further comprising providing a solid stationary phase having a chiral orientation for retaining the undesired enantiomer.

15. The process of claim 1 wherein the metal-organic complex has an organic ligand which is a nitrogen containing heterocycle which confers chirality to the metal-organic complex.

16. The process of claim 15 wherein the organic ligand is 2,2-dipyridine.

17. The process of claim 15 wherein the organic ligand is 1,10-phenanthroline.

* * * * *